United States Patent [19]
Deutsch et al.

[11] Patent Number: 5,959,188
[45] Date of Patent: Sep. 28, 1999

[54] METHOD AND APPARATUS FOR TESTING OF CARBON MONOXIDE DETECTORS

[75] Inventors: Robert D. Deutsch, Wyoming, Ohio; James C. Wantz, Mesa, Ariz.

[73] Assignee: Leon Cooper, Malibu, Calif.

[21] Appl. No.: 08/986,928

[22] Filed: Dec. 8, 1997

[51] Int. Cl.⁶ .................................................. G01N 1/22
[52] U.S. Cl. ............................ 73/1.06; 73/1.02; 340/515
[58] Field of Search .................... 73/1.01, 1.02, 73/1.03, 1.05, 1.06; 340/514, 515, 632

[56] References Cited

U.S. PATENT DOCUMENTS

| | | |
|---|---|---|
| 3,242,715 | 3/1966 | Hubner ...................................... 73/1.03 |
| 4,017,414 | 4/1977 | Black et al. . | |
| 4,522,190 | 6/1985 | Kuhn et al. . | |
| 5,117,809 | 6/1992 | Scaringe et al. . | |
| 5,335,534 | 8/1994 | Wong ....................................... 73/1.07 |
| 5,420,440 | 5/1995 | Ketler et al. ......................... 340/630 X |
| 5,443,056 | 8/1995 | Smith et al. . | |
| 5,611,620 | 3/1997 | Wantz ......................................... 374/1 |
| 5,659,125 | 8/1997 | Ernst ....................................... 73/1.03 |

*Primary Examiner*—Daniel S. Larkin
*Attorney, Agent, or Firm*—Natan Epstein

[57] ABSTRACT

A method for operationally testing a wall mounted electronic carbon monoxide detector by temporarily hanging a test enclosure over the installed carbon monoxide detector so as to define a closed space between the test enclosure and the wall surface, and introducing a test gas into the enclosed space to determine the operational status of the detector. Hydrogen gas may be used as the test gas and generated by wetting a wafer of supercorroding alloy in the enclosure.

19 Claims, 1 Drawing Sheet

METHOD AND APPARATUS FOR TESTING OF CARBON MONOXIDE DETECTORS

BACKGROUND OF THE INVENTION

1. Field of the Invention

This invention concerns a method and apparatus for operational testing of electronic carbon monoxide detectors.

2. State of the Prior Art

Electronic carbon monoxide detectors are coming into widespread use and many such units have been installed by concerned home owners. Carbon monoxide is an odorless, colorless gas generated by certain combustion processes. For example, carbon monoxide frequently is an undesirably by-product of kerosene and fuel oil heaters, which if improperly vented to the outside atmosphere, can cause dangerous and occasionally lethal accumulations of carbon monoxide in an enclosed space. The unfortunate result is that every year many persons die from carbon monoxide poisoning. Installation of carbon monoxide detectors on premises which are at particular risk of accumulation of that gas can save lives by providing early warning of unusual levels of the gas before dangerous concentrations have a chance to build up. Recent advances in detector technology has brought about the commercial availability of compact, affordable electronic carbon monoxide detectors, suitable for home use.

A shortcoming of these carbon monoxide detectors is the lack of means for operationally testing these units, that is, testing the actual response of the electronic detector to the presence of carbon monoxide in the environment. Instead, the commercially available carbon monoxide detectors commonly are equipped with a test button which when actuated serves to verify the operation of the electronic circuits and of the audible or visual signaling system. This type of testing does not, however, verify the proper operation of the gas sensor element of the detector unit, i.e., the test does not verify that the gas sensor and associated detector circuits are capable of responding to the actual presence of carbon monoxide gas in the immediate environment. Clearly, this is a serious shortcoming as proper operation of the gas sensor element is critical to the usefulness of the detector unit as a whole. Proper operation of the remaining electronics and the audio signaling device is meaningless in the absence of a properly functioning gas sensor.

What is needed is a simple, inexpensive, and reliable method and apparatus for testing carbon monoxide detectors in such manner as to verify the proper operation and actuation of the carbon monoxide gas sensor in the presence of that gas in the immediate environment. Also, the desired method and apparatus should be safe and easy to implement by the ordinary home owner.

SUMMARY OF THE INVENTION

The present invention addresses the aforementioned need by providing a method for testing electronic carbon monoxide detectors by generating a free gas other than carbon monoxide yet capable of actuating a commercial carbon monoxide detector when sensed by the gas sensor of that detector.

It is known that the sensor of a carbon monoxide detector is sensitive to gases other than the carbon monoxide gas which it is intended to detect. This knowledge, however, has never been exploited for the purpose of functionally testing carbon monoxide detectors by exposure to such other gas, in effect simulating the presence of carbon monoxide gas.

The present invention broadly contemplates the operational testing of electronic carbon monoxide detectors by exposing the detectors to a test gas other than carbon monoxide. This is generally accomplished by providing a temporary enclosure about the detector unit to be tested without disturbing the existing installation of the detector unit, and releasing the test gas into the temporary enclosure.

The operational testing according to this invention may be conveniently carried out with the aid of a test enclosure which may be temporarily placed over an existing installed carbon monoxide detector for carrying out the operational test. The test enclosure may include a reaction compartment in which a gas generating composition can be chemically reacted. The test enclosure serves to define a substantially enclosed volume for containing the test gas to achieve a sufficient concentration for a sufficient length of time to bring about activation of the detector. The test gas may be generated by means of a chemical reaction or may be released from a separate container holding a supply of the test gas such as a compressed gas bottle.

The temporary enclosure may be provided by placing the test enclosure over the detector unit and against a supporting surface to which the detector unit is normally mounted, typically an interior wall surface. The test enclosure together with the supporting surface define a substantially closed volume which contains the detector unit to be tested. The test enclosure may be conveniently supported against the wall surface simply by hanging on the installed detector unit. The enclosure may take the form of a rectangular pan shape with a top, bottom, two-sides, and a front. The rear of the test enclosure is preferably open so that the enclosure can be placed over the detector unit under test and against the supporting surface. The enclosure may be suspended by placing the top of the enclosure on the top of the detector unit. Part or all of the test enclosure may be transparent to permit visual observation of the test process, and in particular, observation of any visual indicators such as LED displays on the carbon monoxide detector unit which may be actuated during the test procedure. The reaction compartment of the test enclosure may be in the form of a small drawer slidable between an open and a closed position in relation to the rest of the enclosure, and may be positioned at the bottom of the test enclosure to allow a lighter than air test gas to rise towards the detector under test.

A presently preferred test gas is hydrogen gas, which can be safely released in the small amounts needed for purposes of this testing. While free hydrogen gas can be generated or introduced in many ways, a presently preferred method for generating the hydrogen gas is by a chemical reaction between a solid reactant and a liquid reactant, such as a solid supercorroding metal alloy with a salt water solution.

The supercorroding alloy may be an alloy of iron and magnesium, preferably formed into gas generating wafers made by sintering finely powdered metal alloy in a porous matrix of thermoplastic material. It is advantageous to include dry salt in the sintered composition so that an electrolytic salt solution is obtained upon wetting of the wafer with water. This type of composition is known and a method for making such porous wafers is described, for example, in U.S. Pat. No. 4,522,190 issued to Kuhn et al. These supercorroding alloy compositions have found use as personal body warmers in cold environments, for underwater divers, campers and the like, and particularly as flameless ration heaters for "meal ready to eat" (MRE) military field rations. Nonetheless, the usefulness of these compositions for the convenient testing of electronic carbon monoxide detectors has remained undiscovered until now.

One or more wafers of the supercorroding alloy may be placed into the reaction compartment of the test enclosure and a quantity of water may be added in order to wet the supercorroding alloy wafer and initiate the hydrogen generating chemical reaction. The wetting may be conveniently achieved with the aid of a disposable syringe filled with the wetting liquid or water.

These and other improvements, features and advantages according to the present invention will be better understood by reference to the following detailed description of the preferred embodiments taken in conjunction with the accompanying drawings.

DETAILED DESCRIPTION OF THE PREFERRED EMBODIMENTS

Figure 1:
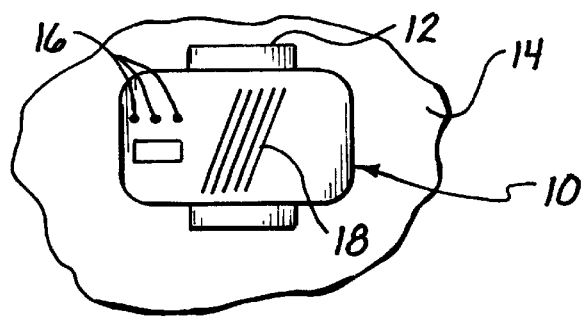
FIG. 1 is a front view of a typical commercially available electronic carbon monoxide detector which is battery operated or plugged into an A.C. power outlet provided in a supporting wall.

With reference to the accompanying drawings in which like numerals designate like elements, FIG. 1 shows a typical electronic carbon monoxide gas detector, generally designated by the numeral 10. Electrical connector prongs on the rear side (not shown in the drawings) of detector 10 plug into a standard A.C. power outlet. The presence of the power outlet is suggested by the top and bottom portions of a face plate 12, such as normally covers power outlets installed in a wall 14. The detector unit 10 shown has a number of LED (light emitting diode) visual indicators 16 on the front of the detector housing, and a series of slits 18 which admit air flow into the detector housing, in which is contained a sensor and conventional electronic circuitry, capable of responding to the presence of carbon monoxide gas in the air. The presence of the carbon monoxide (CO) gas results in generation of an electrical output signal by the gas sensor, which signal activates suitable electronic circuits resulting in the generation of visual and/or audible alarm signals intended to alert persons in the vicinity to the presence of dangerous levels of carbon monoxide gas. The illustration in FIG. 1 is suggestive of only one type of commercially available electronic CO detectors. Other CO detectors are available having an exterior appearance different from that shown in FIG. 1. Furthermore, not all commercially available detectors are intended to mount directly over an existing AC power outlet. Some detectors are provided with an AC power cord or are battery operated so that the detector unit may be mounted remotely to an existing outlet, where no AC power outlet is correctly situated for proper operation of the CO detector. Carbon monoxide is a heavier than air gas and CO detectors normally should be mounted at a relatively low level above a floor or ground surface so as to sense buildups of carbon monoxide at an early stage.

Figure 3:
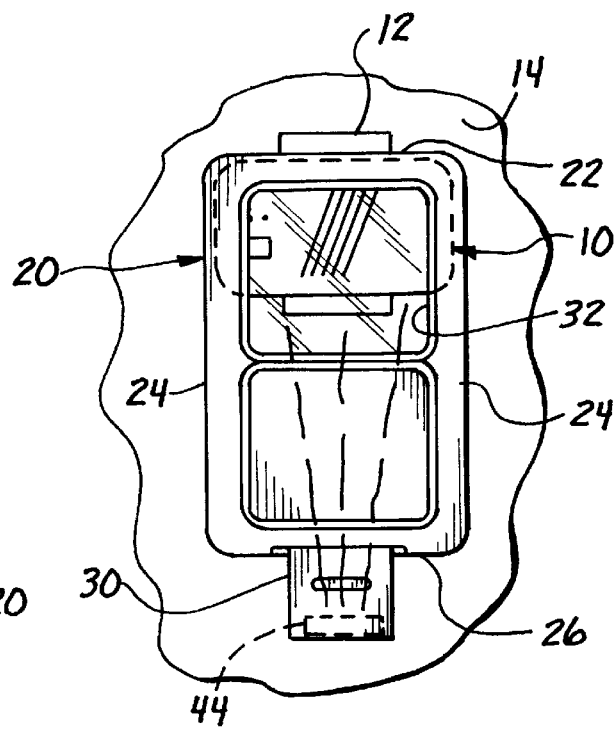
FIG. 3 is a frontal view of the test enclosure of FIG. 2, with phantom lining suggesting hydrogen gas rising from the wafer in the closed reaction compartment towards the carbon monoxide detector being tested.
Figure 2:
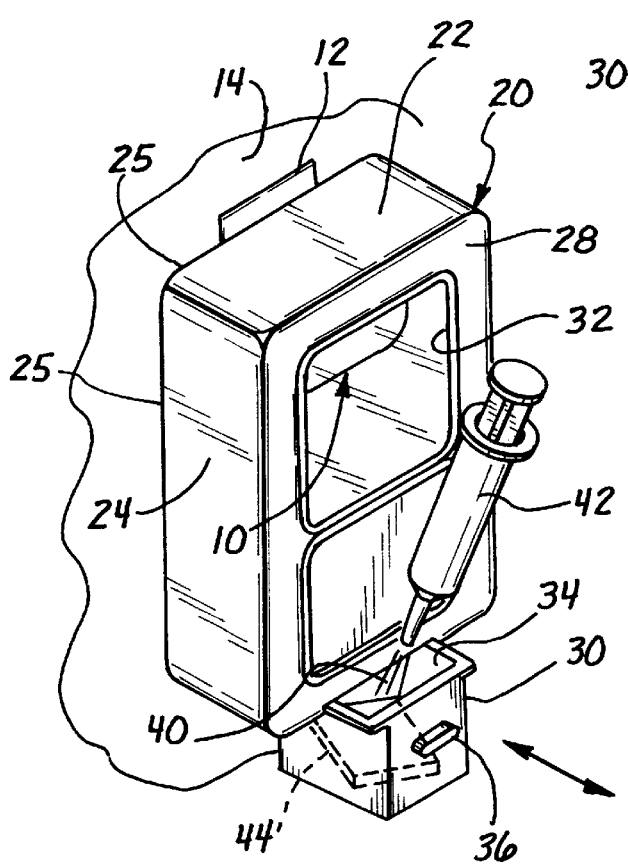
FIG. 2 is a perspective view of the test enclosure suspended on the carbon monoxide detector of FIG. 1, and illustrates the wetting of the hydrogen generating wafer by addition of water from a syringe into the open reaction compartment of the enclosure.

The apparatus employed in the practice of this invention is shown in FIG. 2, and includes a test enclosure 20 which is generally pan shaped with a transparent top 22, two-sides 24, and a bottom 26, better seen in FIG. 3. The test housing also has a front 28 which has a transparent window 32. At the bottom of the test enclosure is a reaction compartment 30 in the form of small rectangular drawer mounted for sliding movement to the bottom 26. The reaction compartment 30 has an open top 34, which is open to the interior of the test enclosure 20 in the closed position of the compartment 30. A small pull tab 36 secured to the front of the compartment 30 facilitates sliding of the compartment as suggested by the bi-directional arrow in FIG. 2, between the open position in FIG. 2 and a closed position illustrated in FIG. 3. The presently preferred dimensions of the enclosure 20 are 10.5 inches in height by 5.5 inches in width by 2.5 inches deep. The size of the reaction compartment 30 is 1.75 inches in height by 2.25 inches in width by 1.25 inches deep. The size of either may be increased or decreased should sizes of product change.

The test enclosure 20 is temporarily placed over the CO detector 10 for test purposes as shown in FIGS. 2 and 3, by hanging or suspending the enclosure 20 on the wall mounted CO detector 10. This is easily and quickly accomplished by simply placing the open rear of the enclosure 20 against the surface of the supporting wall 14 as best seen in FIG. 2. The rear edges 25 of the enclosure generally make contact with the wall surface to substantially close the interior of the test enclosure against free airflow into or out of the enclosure 20. Although the enclosure does not make a positive airtight seal with the wall surface, the degree of containment achieved by simply placing the enclosure against the wall surface is sufficient for purposes of this test procedure.

After placing the test enclosure 20 as just described, a test gas is introduced into the test enclosure. The test gas may be any gas other than carbon monoxide capable of actuating the detector unit 10, and the test gas may be introduced into the enclosure by any convenient means, including release of the test gas from a compressed gas bottle or by chemical generation of the free gas.

By way of example, and as the presently preferred form of practicing this invention, free hydrogen gas is generated by adding water 40, for example, by means of a disposable plastic syringe 42, to a gas generating wafer 44 placed in the reaction compartment 30. The wafer 44 contains a supercorroding metal alloy, preferably a magnesium-iron alloy, as well as dry salt, all contained in a porous matrix of thermoplastic material. Suitable wafers can be manufactured as disclosed in the previously mentioned U.S. Pat. No. 4,522, 190, or by any other known method for manufacturing so called flameless ration heaters used in MRE military field rations. The dimensions of the wafer 44 as presently used are 1.25 by 0.75 inches by ⅜ inch or less in thickness, although these dimensions are not critical.

Addition of the water 40 dissolves dry salt in the wafer 44, producing a sodium chloride solution which wets the supercorroding alloy particles suspended in the porous matrix. The metal alloy reacts with the salt solution in a well known manner, as described for example in the aforementioned U.S. Pat. No. 4,522,190 and references cited therein, producing free hydrogen gas as a by-product of the reaction. Once the water 40 has been added, the reaction compartment 30 is slid towards the wall 14 to the closed position as in FIG. 3. It should be appreciated that neither the size of the wafer 44 nor the amount of water 40 added to the wafer are critical to this test procedure, since a sufficient amount of free hydrogen will be produced with a relatively wide range of wafer dimensions and amount of added water.

The free hydrogen gas generated by the wet wafer 44, being lighter than air, rises readily into the test housing 28 and towards the CO detector unit 10. As the hydrogen gas enters the housing of the detector unit 10 and comes into contact with the gas sensing element inside the unit, a properly functioning gas sensor will be actuated by the hydrogen gas causing the detector unit 10 to go into an alarm condition and triggering such audible and/or visual indicators as the particular detector unit may have. The operational status of the detector unit under test is determined by observing its response or lack of it to the presence of the test gas in the test enclosure.

Most commercial consumer grade electronic carbon monoxide detectors have a relatively slow response time to the presence of carbon monoxide gas. These detectors have a time delay built into the alarm circuit which allows the unit to "purge" its sensing system. Ambient levels of carbon monoxide are detected and stored in a memory of the detector circuit during this "purge" time, and are compared to previously stored acceptable reference levels. Ambient readings are taken and compared with reference levels in successive cycles until the ambient readings exceed the stored reference levels, in which case an alarm condition is activated. Each cycle may range from as little as 3–4 minutes in some commercial detectors while others may require as along as 8–10 minutes for the same purpose. In either case, the person carrying out this test procedure must allow a sufficient length of time to pass after the wafer 44 has been wetted and the compartment 30 closed. If after allowing ample time for the detector 10 to react to the simulated presence of carbon monoxide by the free hydrogen gas in the test enclosure 20, and no alarm indication is produced by the detector unit 10, the detector unit should be suspected of being defective, calling for closer inspection or replacement of the detector unit 10.

Once the detector 10 has been adequately tested, the test enclosure 20 is simply removed from the detector 10 and can be carried to the next CO detector to be tested, if any.

If the CO detector unit 10 under test has a particularly long delay in its response, it may be necessary to add more water to the wafer 44, or to place a fresh wafer 44 along with an additional tablespoon or so of water, in order to maintain a sufficient concentration of hydrogen gas within the test enclosure 20 until the detector unit 10 completes its CO gas sensing cycle.

Some CO detectors are equipped with a digital readout which displays sensed CO levels. The digital display on such a detector unit will indicate that the detector is responding to increasing concentrations of hydrogen gas in the test enclosure 20 before reaching actual alarm status. In such case, the test procedure may be cut short by removing the test enclosure 20 once proper operation of the gas sensing element has been verified by activity on the digital display, but before an alarm is sounded by the detector unit.

It will be understood that the particular shape, size and arrangement of the test housing 20 and reaction compartment 30 are not critical to the present invention, and other enclosures and devices for containing and sustaining a sufficient level of free hydrogen gas about the CO detector under test can be devised and used with comparable efficacy. The invention also contemplates the use of gas generating wafers lacking dry salt and where the reaction is initiated by addition of a salt solution as the wetting liquid rather than water alone. Also, other metal pairs may be combined to make hydrogen generating supercorroding metal alloys, such as Magnesium-Titanium, Magnesium-Nickel, Magnesium-Copper and Magnesium-Carbon. The present invention should not be limited to the use of super corroding alloys, as free hydrogen gas can be conveniently generated by means of other types of chemical reactions, such as by reacting a metal-acid pair, for example, zinc with hydrochloric acid.

From the foregoing it will be appreciated that, while a presently preferred embodiment of the invention has been described and illustrated for purposes of clarity and example, many changes, substitutions and modifications to the described embodiment will be apparent to those having ordinary skill in the art without thereby departing from the scope and spirit of the present invention, which is defined by the following claims.

What is claimed is:

1. A method for operationally testing an electronic carbon monoxide detector installed on a supporting surface, comprising the steps of:

temporarily hanging a test enclosure over the installed carbon monoxide detector and against the said supporting surface so as to define a substantially closed volume between the test enclosure and the supporting surface which volume contains the detector;

introducing a test gas other than carbon monoxide but capable of activating the carbon monoxide detector into said temporary enclosure at a sufficient concentration and for a length of time normally sufficient to activate the carbon monoxide detector thereby to determine the operational status of the detector; and removing the temporary enclosure.

2. The method of claim 1 wherein said test gas is hydrogen gas.

3. The method of claim 1 wherein said step of introducing a test gas comprises the steps of providing in said test enclosure a supply of a supercorroding metal alloy of the type reactive with a salt solution for generating free hydrogen gas, placing said metal alloy in proximity to an electronic carbon monoxide detector to be tested, and reacting said metal alloy with an amount of said salt solution so as to expose the detector to free hydrogen gas generated by the reaction.

4. The method of claim 3 wherein said supercorroding alloy is an alloy of magnesium and iron.

5. The method of claim 3 wherein said supply of supercorroding metal alloy is in the form of one or more wafers made by forming the supercorroding alloy in a porous matrix of polymer material.

6. The method of claim 5 wherein said wafer contains dry salt such that said salt solution is produced by wetting said wafer with water.

7. A method of testing an electronic carbon monoxide detector comprising the steps of placing a test enclosure about a carbon monoxide detector to be tested, said test enclosure having a reaction compartment for holding a supply of chemical reactants below the carbon monoxide detector to be tested, and placing in said compartment a supply of chemical reactants selected for chemically releasing a test gas capable of actuating a normally functioning electronic carbon monoxide detector.

8. The method of claim 7 wherein said test gas is hydrogen gas.

9. The method of claim 7 wherein the carbon monoxide detector to be tested is mounted on a supporting surface and said test enclosure is temporarily placed over the detector and against the supporting surface.

10. The method of claim 9 wherein the supporting surface is a wall surface and the test enclosure is placed by suspending said enclosure on the detector against the wall surface.

11. The method of claim 10 wherein said reaction chemical reactants comprise a solid component and a liquid component, and further comprising the step of reacting said chemical reactants by adding said liquid component to said solid component in said compartment while the test enclosure is suspended on the detector.

12. The method of claim 11 wherein said reaction compartment is movable between an open and a closed position relative to the test enclosure, and said step of adding comprises moving the compartment to the open position, adding the liquid component, and moving the compartment to the closed position for containing the test gas within the test enclosure.

13. The method of claim 12 wherein said solid component comprises a supercorroding metal alloy and the liquid component comprises water.

14. A method for testing a wall mounted electronic carbon monoxide detector, comprising the steps of:

placing a test enclosure having a rear adapted to be placed against a wall on which is supported an electronic carbon monoxide detector to be tested, said rear being open for admitting the detector into said enclosure while generally contacting the wall about the detector thereby to close said enclosure against significant airflow into or out of the enclosure;

supporting said test enclosure by temporarily hanging said enclosure from the detector;

providing at least one gas generating wafer containing supercorroding magnesium-iron alloy and dry sodium chloride in a porous matrix of polymer material;

wetting said wafer with water so as to release free hydrogen gas into said test enclosure for simulating the presence of carbon monoxide gas;

waiting a sufficient period of time to determine the response if any of the detector to the presence of the gas; and removing said test enclosure away from said wall and the detector.

15. Apparatus for testing a wall mounted electronic carbon monoxide detector, comprising:

a test enclosure adapted to be hung from the said carbon monoxide detector and having an enclosure rear open for admitting the detector into said enclosure while generally contacting the wall about the detector thereby to define with the wall a substantially closed space about the detector, said test enclosure having a reaction compartment in communication with said closed space for holding chemical reactants selected for releasing a test gas into said substantially closed space.

16. The apparatus of claim 15 wherein said chemical reactants comprise at least one gas generating wafer containing a supercorroding metal pair and a salt solution.

17. The apparatus of claim 15 wherein said chemical reactants comprise a metal and an acid.

18. The apparatus of claim 15 wherein said test gas is hydrogen gas.

19. A kit for testing wall a mounted electronic carbon monoxide detector, comprising:

a test enclosure adapted to be hung from the said carbon monoxide detector and having an enclosure rear open for admitting the detector into said enclosure while generally contacting the wall about the detector thereby to define with the wall a substantially closed space about the detector, said test enclosure having a reaction compartment in communication with said substantially closed space for holding chemical reactants selected for releasing a test gas into said substantially closed space;

a supply of chemical reactants selected for generating upon being wetted with a liquid a test gas other than carbon monoxide capable of activating the carbon monoxide detector; and a disposable syringe for dispensing the liquid onto said chemical reactants thereby to release said test gas into said substantially closed space such that the response of the said detector to said test gas may be determined.

* * * * *